United States Patent [19]

Watanabe et al.

[11] Patent Number: 5,227,510
[45] Date of Patent: Jul. 13, 1993

[54] METHOD FOR PRODUCING A CARBONIC ACID ESTER

[75] Inventors: Eiichi Watanabe, Kanagawa; Kenji Murayama, Yokohama; Kazutaka Ida, Yokohama; Keisuke Wada, Yokohama; Yukio Kasori, Yokkaichi, all of Japan

[73] Assignee: Mitsubishi Kasei Corporation, Tokyo, Japan

[21] Appl. No.: 918,025

[22] Filed: Jul. 24, 1992

[30] Foreign Application Priority Data

Sep. 17, 1991 [JP] Japan ............... 3-236546
Mar. 11, 1992 [JP] Japan ............... 4-52786

[51] Int. Cl.⁵ .................................... C07C 69/96
[52] U.S. Cl. ......................................... 558/277
[58] Field of Search .............................. 558/277

[56] References Cited

U.S. PATENT DOCUMENTS

| Re. 29,338 | 8/1977 | Perrotti et al. | 558/277 |
| 3,994,960 | 11/1976 | Yamazaki et al. | 558/277 |
| 4,361,519 | 11/1982 | Hallgren | 558/277 |
| 4,370,275 | 1/1983 | Stammann et al. | 558/277 |
| 5,004,827 | 4/1991 | Curnutt | 558/277 |

FOREIGN PATENT DOCUMENTS

0354970 2/1990 European Pat. Off.

Primary Examiner—José G. Dees
Assistant Examiner—Dwayne C. Jones
Attorney, Agent, or Firm—Oblon, Spivak, McClelland, Maier & Neustadt

[57] ABSTRACT

A method for producing a carbonic acid ester, which comprises reacting an aliphatic alcohol with carbon monoxide and oxygen in the presence of ① a platinum group metal or its salt, ② metal copper, a copper salt or a copper complex, ③ at least one member selected from the group consisting of alkali metal salts and alkaline earth metal salts, and ④ a 2-hydroxypyridine.

20 Claims, No Drawings

METHOD FOR PRODUCING A CARBONIC ACID ESTER

The present invention relates to a method for producing a carbonic acid ester which is industrially useful as an intermediate for the production of polycarbonates, as an intermediate for medicines or agricultural chemicals, or as a solvent.

As a method for producing a carbonic acid ester, there is a method wherein an alcohol and phosgene are reacted to produce a carbonic acid ester. However, this method has problems such that phosgene has strong toxicity, electrolytic chlorine required for the production of phosgene is expensive, and highly corrosive hydrochloric acid is produced as a byproduct by the reaction with the alcohol and phosgene.

As a method wherein no phosgene is used, there is a method wherein an alcohol is reacted with carbon monoxide and oxygen in the presence of a copper salt catalyst (Japanese Examined Patent Publication No. 58739/1985). However, this method has problems such that a combustion loss of carbon monoxide is substantial, and the reaction rate is low. Further, a method is known wherein an alcohol is reacted with carbon monoxide and oxygen in the presence of a catalyst system comprising palladium, a copper salt and an amine, instead of the copper catalyst (Japanese Examined Patent Publications No. 8816/1986 and No. 43338/1986), but this method has a problem such that a combustion loss of carbon monoxide is substantial. Further, a method is also known wherein a carbonic acid ester is produced by reacting an alcohol with carbon monoxide and an oxidizing agent in the presence of a catalyst system comprising palladium, a copper salt and pyridine (Japanese Unexamined Patent Publication No. 4737/1990). However, no adequate solution has been obtained with respect to the loss due to combustion of carbon monoxide.

Further, such methods for the production in a liquid phase tend to have a problem that it is difficult to separate the formed product from the catalyst. In an attempt to solve this problem, a method has been proposed in which a carbonic acid ester is produced by reacting nitrous acid ester with carbon monoxide in a gas phase in the presence of a solid catalyst having a second metal such as iron, copper or bismuth added to a platinum group metal (Japanese Unexamined Patent Publication No. 141243/1991). However, no adequate reaction rate is thereby obtainable, and the process is cumbersome, for example, in that steps for recovering and regenerating the nitrous acid ester are required.

It is an object of the present invention to provide a method for producing a carbonic acid ester at an industrially applicable high reaction rate by a reaction to obtain a carbonic acid ester from an alcohol, carbon monoxide and oxygen, while reducing a deterioration of the selectivity for carbon monoxide due to e.g. a combustion loss.

Another object of the present invention is to provide an industrially advantageous method for producing a carbonic acid ester from an alcohol, carbon monoxide and oxygen by a gas phase method where no step for separating the catalyst and the formed product is required.

The present inventors have conducted extensive researches for a cocatalyst in the reaction to obtain a carbonic acid ester from an alcohol, carbon monoxide and oxygen by means of a platinum group metal-copper type catalyst and as a result, have found it possible to substantially reduce a deterioration of the selectivity due to e.g. a combustion loss of carbon monoxide and to improve the production rate of a carbonic acid ester, by adding a 2-hydroxypyridine in the presence of at least one member selected from the group consisting of alkali metal salts and alkaline earth metal salts. The present invention has been accomplished on the basis of this discovery. Further, it has been found that similar effects can be obtained also by using a complex compound made of a platinum group metal salt and a 2-hydroxypyridine. The operational mechanism of 2-hydroxypyridines has not yet been clearly understood. However, it is believed that such excellent effects are derived from a combination of the strength of the acid-base of 2-hydroxypyridines and the steric distance between the acid and the base. Further, separation of the catalyst and the formed product can be facilitated by conducting the reaction in a gas phase using a solid catalyst having the above-mentioned catalyst components supported on a carrier.

Thus, according the first aspect, the present invention provides a method for producing a carbonic acid ester, which comprises reacting an aliphatic alcohol with carbon monoxide and oxygen in the presence of ① a platinum group metal or its salt, ② metal copper, a copper salt or a copper complex, ③ at least one member selected from the group consisting of alkali metal salts and alkaline earth metal salts, and ④ a 2-hydroxypyridine.

According to the second aspect, the present invention provides a method for producing a carbonic acid ester, which comprises reacting an aliphatic alcohol with carbon monoxide and oxygen in the presence of ① a complex compound made of a platinum group metal or its salt and a 2-hydroxypyridine, ② metal copper, a copper salt or a copper complex, and ③ at least one member selected from the group consisting of alkali metal salts and alkaline earth metal salts.

According to the third aspect, the present invention provides a method for producing a carbonic acid ester, which comprises reacting an aliphatic alcohol with carbon monoxide and oxygen in the presence of ① a complex compound made of a platinum group metal or its salt and a 2-hydroxypyridine, ② metal copper, a copper salt or a copper complex, ③ at least one member selected from the group consisting of alkali metal salts and alkaline earth metal salts, and ④ a 2-hydroxypyridine.

According to the fourth aspect, the present invention provides a method for producing a carbonic acid ester, which comprises reacting an aliphatic alcohol with carbon monoxide and oxygen in a gas phase in the presence of a solid catalyst having supported on a carrier ① a complex compound made of a platinum group metal or its salt and a 2-hydroxypyridine, ② metal copper, a copper salt or a copper complex, and ③ at least one member selected from the group consisting of alkali metal salts and alkaline earth metal salts.

According to the fifth aspect, the present invention provides a method for producing a carbonic acid ester, which comprises reacting an aliphatic alcohol with carbon monoxide and oxygen in a gas phase in the presence of a solid catalyst having supported on a carrier ① a platinum group metal or its salt, ② metal copper, a copper salt or a copper complex, ③ at least one member selected from the group consisting of alkali metal salts and alkaline earth metal salts, and ④ a 2-hydroxypyridine.

Now, the present invention will be described in detail with reference to the preferred embodiments.

The method of the present invention can be conducted in a liquid phase or in a gas phase. In the following description, the method will be described mainly with respect to a liquid phase reaction.

As the platinum group metal useful in the present invention, ruthenium, rhodium, palladium, iridium or platinum may, for example, be mentioned. Among them, palladium is preferred. These metals may be used as single substances or in the form of their salts such as halides, nitrates, sulfates, phosphates or acetates. More specifically, ruthenium chloride, ruthenium iodide, ruthenium tris(acetylacetonate), rhodium chloride, rhodium bromide, rhodium iodide, rhodium nitrate, rhodium sulfate, rhodium acetate, palladium chloride, palladium bromide, palladium iodide, palladium acetate, palladium propionate, palladium nitrate, palladium sulfate, palladium phosphate, palladium bis(acetylacetonate), palladium oxalate, iridium chloride, chloroplatinic acid or potassium tetrachloroplatinate, may, for example, be mentioned.

Further, it may be used in the form supported on a carrier such as active carbon, graphite, alumina, silica, silica-alumina, diatomaceous earth, asbestos, ion exchange resin, calcium silicate, aluminosilicate, polyvinylpyridine or magnesium oxide. The platinum group metal or its salt is generally used in an amount within a range of from 0.001 to 100 mmol, preferably from 0.01 to 100 mmol per liter of the aliphatic alcohol.

Among the metal copper, the copper salt and the complex compound of copper to be used in the present invention, the copper salt may not only be a halide such as cupric chloride or cuprous chloride, but also a nitrate, a sulfate, an aliphatic carboxylic acid salt such as copper acetate or copper propionate, an aromatic carboxylic acid salt such as copper benzoate, or a phosphate. The complex compound of copper is a complex salt with an organic ligand, for example, a complex salt with an organic ligand having a nitrogen atom, an oxygen atom, or nitrogen and oxygen atoms. More specifically, as the organic ligand having a nitrogen atom, an aliphatic amine such as triethylamine, an aromatic amine such as aniline, a diamine such as tetramethylethylenediamine, a pyridine, an imidazole or a quinoxaline, may, for example, be mentioned. As the organic ligand having an oxygen atom, an N-oxide, a $\beta$-diketone, a salicylic acid derivative or a dicarboxylic acid, may, for example, be mentioned. As the organic ligand having nitrogen and oxygen atoms, a hydroxypyridine, a hydroxyquinoline or a hydroxyaniline, may, for example, be mentioned. Preferred is a 2-hydroxypyridine, a 2-methoxypyridine, a 4-cyanopyridine, a tetraalkyldiaminoalkane or a quinoxaline. Particularly preferred is 2-hydroxypyridine.

Such metal copper, a copper salt or a copper complex is generally used in an amount within a range of from 1 to $10^5$ mols, preferably from 1 to $10^4$ mols, more preferably from 1 to $10^3$ mols, per mol of the platinum group metal atoms.

The alkali metal salt or the alkaline earth metal salt may, for example, be an alkali metal salt such as a lithium salt, a sodium salt, a potassium salt or a cesium salt, or an alkaline earth metal salt such as a magnesium salt, a calcium salt or a barium salt, of an organic acid, e.g. an aliphatic carboxylic acid such as acetic acid, propionic acid, butyric acid, valeric acid or caproic acid, or an inorganic acid such as carbonic acid, nitric acid or phosphoric acid; or an alkali metal halide such as sodium chloride, potassium chloride, lithium chloride or cesium chloride, or an alkaline earth metal halide such as magnesium chloride, calcium chloride or barium chloride. Such an alkali metal salt or an alkaline earth metal salt is used usually within a range of from 1 to $10^5$ mols, preferably from 1 to $10^4$ mols, per mol of the platinum group metal atoms.

The 2-hydroxypyridine may have on the 2-hydroxypyridine ring a substituent which does not adversely affect the present invention, such as an alkyl group, an alkoxy group or a halogen atom. Specifically, 2-hydroxypyridine, 2-hydroxy-4-methylpyridine, 2-hydroxy-6-methylpyridine, 2-hydroxy-4-ethylpyridine, 2-hydroxy-4-methoxypyridine, 2-hydroxy-6-methoxypyridine, 4,6-dimethyl-2-hydroxypyridine, 2-hydroxy-4-chloropyridine, or 2-hydroxy-6-chloropyridine, may, for example, be used. Preferred is 2-hydroxypyridine or a 2-hydroxyalkylpyridine such as 2-hydroxy-6-methylpyridine. The 2-hydroxypyridine is generally used in an amount within a range of from 1 to $10^4$ mols, preferably from 1 to $10^3$ mols, per mol of the platinum group metal atoms.

The complex compound made of a platinum group metal or its salt and a 2-hydroxypyridine is a complex compound having the 2-hydroxypyridine coordinated by its nitrogen atom to the platinum group metal, and it may, for example, be bis(2-hydroxypyridine)palladium chloride, bis(2-hydroxypyridine)palladium bromide or bis(2-hydroxypyridine)palladium diacetate. Such a complex compound may be synthesized in the reaction system for the production of a carbonic acid ester by adding a for reaction, or such a complex compound may be preliminarily synthesized and isolated and then added to the reaction system for the production of a carbonic acid ester. With respect to a common method for producing this complex compound, for example, bis(2-hydroxypyridine)palladium chloride can be prepared by dissolving palladium chloride and sodium chloride in methanol and then adding 2-hydroxypyridine thereto. The complex compound made of a platinum group metal or its salt and a 2-hydroxypyridine, is generally used in an amount within a range of from 0.001 to 100 mmol, preferably from 0.01 to 100 mmol, per liter of the aliphatic alcohol.

Even when such a complex compound is used, it is preferred to use 2-hydroxypyridine as well from the viewpoint of the stability of the catalyst. In such a case, 2-hydroxypyridine is generally used in an amount within a range of from 1 to $10^4$ mols, preferably from 1 to $10^3$ mols, per mol of the platinum group metal atoms.

In the method of the present invention, a side-reaction preventive agent e.g. a quaternary ammonium salt such as tetramethylammonium chloride, tetra-n-butylammonium chloride, tetra-n-butylammonium iodide, tri-n-octylmono-n-propylammonium iodide, tetra-n-octylammonium iodide or tetra-n-butylammonium bromide, or a tertiary sulfonium salt such as trimethylsulfonium iodide or triethylsulfonium bromide, may be used for the purpose of controlling formation of carbon dioxide as a byproduct by combustion of carbon monoxide. Such a side-reaction preventive agent may suitably be used in an amount of from 1 to $10^3$ mols per mol of the platinum group metal atoms.

The aliphatic alcohol is preferably a saturated aliphatic alcohol, more preferably a $C_{1-6}$ saturated aliphatic alcohol such as methanol, ethanol, butanol, ethylene glycol, propylene glycol or 1,4-butanediol. Such an alcohol is generally used in an excess amount, since it also serves as a solvent.

In the method of the present invention, it is usual to employ an excess amount of an aliphatic alcohol which serves also as a solvent, as mentioned above. However, a solvent inert to the reaction may separately be used. Specifically, an aromatic hydrocarbon such as benzene, toluene or xylene, a halogenated aromatic hydrocarbon such as chlorobenzene, dichlorobenzene or trichlorobenzene, an aliphatic saturated hydrocarbon such as octane or decane, an ether such as tetrahydrofuran or 1,4-dioxane, an ester such as ethyl acetate or methyl benzoate, a nitrile such as acetonitrile or benzonitrile, an amide such as N-methylpyrrolidone or N,N-dimethylacetamide, or an urea such as ethylene dimethylurea, may be mentioned.

When the method of the present invention is conducted in a liquid phase, the partial pressure of carbon monoxide is usually within a range of from 1 to 50 kg/cm$^2$, preferably from 1 to 30 kg/cm$^2$, and the partial pressure of oxygen is usually within a range of from 0.1 to 20 kg/cm$^2$, preferably from 0.1 to 10 kg/cm$^2$. Carbon monoxide and oxygen to be used may be pure materials. However, they may be used also as diluted with a gas inert to the reaction, such as nitrogen or argon. It is particularly advisable to control the oxygen partial pressure so that the gas composition in the reaction system is outside the explosive range.

The reaction of the present invention is conducted within a temperature range of from 30° to 200° C., preferably from 60° to 150° C., for from 30 minutes to 20 hours.

The reaction may be conducted in a batch system, a gas flow system or a gas-liquid flow system. However, a gas-flow system is preferred, since a high carbonic acid ester-forming rate can thereby be obtained. From the reaction solution, the catalyst, etc. are separated and recovered, and then the carbonic acid ester is recovered by an operation such as distillation or extraction.

In the foregoing, the present invention has been described primary with respect to the liquid phase reaction. However, the reaction of the present invention can also be conducted by a gas phase reaction. The type and amount of the catalyst as well as the conditions of the reaction system are generally the same as in the case of the liquid phase reaction except for the following conditions.

Namely, when the platinum group metal or its salt is used as supported on a carrier, the amount supported on the carrier is usually from 0.01 to 10% by weight, more preferably from 0.1 to 5% by weight, as metal of the platinum group metal, relative to the carrier. The same applies to a case where the platinum group metal or its salt forms a complex compound with a 2-hydroxypyridine.

The metal copper, the copper salt or the complex compound of copper is generally used in an amount within a range of from 1 to 100 mols, preferably from 1 to 20 mols per mol of the platinum group metal atoms.

The 2-hydroxypyridine is generally used in an amount within a range of from 1 to 10$^3$ mols, preferably from 1 to 100 mols, per mol of the platinum group metal atoms.

The alkali metal salt or the alkaline earth metal salt is generally used in an amount within a range of from 1 to 10$^3$ mols, preferably from 1 to 200 mols, per mol of the platinum group metal atoms. In the case of a gas phase reaction, the catalyst is preferably used in the form supported on a carrier. As such a carrier, active carbon, graphite, alumina, silica, silica-alumina, diatomaceous earth, asbestos, ion exchange resin, calcium silicate, aluminosilicate, polyvinylpyridine, magnesia, titania or zirconia, may, for example, be mentioned.

A method for supporting on the carrier ① the platinum group metal or its salt (hereinafter referred to as the first component), ② the metal copper, the copper salt or the copper complex (hereinafter referred to as the second component), ③ at least one member selected from the group consisting of alkali metal salts and alkaline earth metal salts (hereinafter referred to as the third component), and ④ the 2-hydroxypyridine (hereinafter referred to as the fourth component), or the complex compound made of the platinum group metal or its salt and the 2-hydroxypyridine (hereinafter referred to as the fifth component), may be a conventional method. For example, it may be a method wherein the first, second and fourth components are dissolved in an organic solvent, the carrier is added thereto for impregnation, followed by drying, and then the third component is likewise supported, or a method wherein the first and second components are firstly supported on the carrier, and then the fourth and third components are sequentially supported. When the fifth component is employed, this component may be supported in a similar manner.

The reaction can be conducted under an ordinary pressure or under an elevated pressure. The partial pressure of carbon monoxide is usually within a range of from 0.001 to 20 kg/cm$^2$, preferably from 0.01 to 10 kg/cm$^2$, and the partial pressure of oxygen is usually within a range of from 0.001 to 10 kg/cm$^2$, preferably from 0.01 to 5 kg/cm$^2$. The partial pressure of the alcohol is usually within a range of from 0.001 to 20 kg/cm$^2$, preferably from 0.01 to 10 kg/cm$^2$.

The reaction can be conducted in a batch system or in a continuous system. However, it is preferred to employ a continuous system wherein the reaction is conducted by continuously supplying carbon monoxide, oxygen and the alcohol to a fixed bed or a fluidized bed where the solid catalyst is present, since a high carbonic acid ester production rate can thereby be obtained. In such a case, the contact time of carbon monoxide, oxygen and the alcohol with the solid catalyst is usually within a range of from 0.04 to 72 seconds, preferably from 0.4 to 7.2 seconds. From the reaction solution, the carbonic acid ester can be recovered by an operation such as distillation or extraction, whereby no cumbersome operation such as separation of the catalyst is required.

Now, the present invention will be described in further detail with reference to Examples. However, it should be understood that the present invention is by no means restricted to such specific Examples.

In the following Examples, the following abbreviations have the following means.

TOF: mols of the carbonic acid ester formed per mol of palladium atoms and per hour of the reaction time (mol/g·atom Pd/hr)

STY: grams of the carbonic acid ester formed per liter of the catalyst and per hour of the reaction time (g/l/hr)

CO selectivity: the carbonic acid ester (mmol)×100/[the carbonic acid ester (mmol)+carbon dioxide (mmol)+2×the oxalic acid ester (mmol)+the acetic acid ester (mmol)+the formic acid ester (mmol)](%)

EXAMPLE 1

In a micro autoclave made of Hastelloy C having an internal capacity of 70 ml, an inner cylinder made of glass was placed, and 0.21 g (0.04 mmol as Pd) of active carbon having 2 wt % of palladium supported thereon (hereinafter referred to simply as 2% Pd/C), 0.5 mmol of cupric acetate, 1.0 mmol of potassium chloride, 0.5 mmol of 2-hydroxypyridine and 10 ml of methanol were introduced thereinto. The interior of the autoclave was thoroughly substituted by carbon monoxide, and then 10 kg/cm$^2$ of carbon monoxide was introduced. Then, 80 kg/cm$^2$ of nitrogen gas containing 3.8 vol % of oxygen was injected. The reaction temperature was set at 80° C., and the reaction was conducted for one hour. Then, the reaction system was cooled to room temperature. After releasing the pressure, the reaction gas and the reaction product solution were analyzed by gas chromatography for a quantitative analysis. The amount of dimethyl carbonate produced was 7.83 mmol; the amount of dimethyl oxalate was 0.01 mmol; the amount of methyl acetate was 0.08 mmol; and the amount of carbon dioxide was 0.99 mmol. Namely, TOF was 196 mol/g.atom Pd/hr, and CO selectivity was 88%.

EXAMPLE 2

The reaction was conducted in the same manner as in Example 1 except that the reaction temperature was raised from 80° C. to 100° C. As a result, 5.47 mmol of dimethyl carbonate, 0 mmol of dimethyl oxalate, 0.04 mmol of methyl acetate and 1.27 mmol of carbon dioxide were formed. Namely, TOF was 137, and CO selectivity was 81%.

COMPARATIVE EXAMPLE 1

The reaction was conducted in the same manner as in Example 2 except that no 2-hydroxypyridine was added. As a result, 3.53 mmol of dimethyl carbonate, 0.43 mmol of dimethyl oxalate, 0.06 mmol of methyl acetate and 2.65 mmol of carbon dioxide were formed. Namely, TOF was 88, and CO selectivity was 50%.

COMPARATIVE EXAMPLE 2

The reaction was conducted in the same manner as in Example 2 except that pyridine was added instead of 2-hydroxypyridine, whereby 2.27 mmol of dimethyl carbonate, 0.13 mmol of dimethyl oxalate, 0.19 mmol of methyl acetate and 8.12 mmol of carbon dioxide were formed. Namely, TOF was 57, and CO selectivity was 21%. From the results, it is evident that with a simple amine such as pyridine, both the reaction rate and the CO selectivity are low.

COMPARATIVE EXAMPLE 3

The reaction was conducted in the same manner as in Example 2 except that 0.5 mmol of 2-methoxypyridine and 0.5 mmol of phenol were added instead of 2-hydroxypyridine, whereby 3.99 mmol of dimethyl carbonate, 0.55 mmol of dimethyl oxalate, 0.06 mmol of methyl acetate and 3.02 mmol of carbon dioxide were formed. Namely, TOF was 100, and CO selectivity was 49%. Thus, it is evident that the effects of 2-hydroxypyridine are not merely due to the addition of an acid and a base.

EXAMPLE 3

The reaction was conducted in the same manner as in Example 2 except that 2-hydroxy-6-methylpyridine was added instead of 2-hydroxypyridine, whereby 4.10 mmol of dimethyl carbonate, 0.28 mmol of dimethyl oxalate, 0.05 mmol of methyl acetate and 2.06 mmol of carbon dioxide were formed. Namely, TOF was 103, and CO selectivity was 63%.

EXAMPLE 4

The reaction was conducted in the same manner as in Example 2 except that 0.2 mmol of tetra-n-butylammonium bromide was further added, whereby 5.50 mmol of dimethyl carbonate, 0 mmol of dimethyl oxalate and 1.10 mmol of carbon dioxide were formed. Namely, TOF was 139, and CO selectivity was 83%.

EXAMPLE 5

Under the same reaction conditions as in Example 4, the reaction was conducted by increasing the amount of 2-hydroxypyridine from 0.5 mmol to 5.0 mmol, whereby 3.90 mmol of dimethyl carbonate, 0 mmol of dimethyl oxalate and 0.84 mmol of carbon dioxide were formed. Namely, TOF was 97, and CO selectivity was 82%.

EXAMPLE 6

Into the same autoclave as used in Example 1, 0.21 g of 2% Pd/C, 0.5 mmol of cupric acetate, 1.0 mmol of potassium chloride, 0.5 mmol of 2-hydroxypyridine and 10 ml of methanol were introduced. The interior of the autoclave was thoroughly substituted by carbon monoxide, and then 10 kg/cm$^2$ of carbon monoxide was introduced. Then, 80 kg/cm$^2$ of nitrogen gas containing 3.8 vol % of oxygen was injected. The reaction temperature was adjusted to 130° C., and the reaction was conducted for one hour. Then, the reaction system was cooled to room temperature, and the quantitative analysis of the product was conducted in the same manner as in Example 1. As a result, 6.52 mmol of dimethyl carbonate, 0 mmol of dimethyl oxalate, 0.01 mmol of methyl acetate and 1.58 mmol of carbon dioxide were formed. Namely, TOF was 163, and CO selectivity was 80%.

COMPARATIVE EXAMPLE 4

The reaction was conducted in the same manner as in Example 6 except that 0.028 mmol of palladium chloride was used instead of Pd/C, 1.4 mmol of cupric chloride was used instead of 0.5 mmol of cupric chloride, 1.87 mmol of tetraethylammonium chloride was used instead of potassium chloride, and 1.88 mmol of 2,6-lutidine was used instead of 2-hydroxypyridine, whereby 2.1 mmol of dimethyl carbonate, 0 mmol of dimethyl oxalate and 8.9 mmol of carbon dioxide were formed. Namely, TOF was 76, and CO selectivity was 19%.

EXAMPLE 7

Into an autoclave, the same catalyst composition solution as used in Example 6 was charged, and after thoroughly substituting with carbon monoxide, 30 kg/cm$^2$ carbon monoxide was introduced. Then, 80 kg/cm$^2$ of nitrogen gas containing 3.8 vol % of oxygen was injected. The reaction temperature was adjusted to 100° C., and the reaction was conducted for one hour. Then, the reaction system was cooled to room temperature, and the quantitative analysis of the product was conducted in the same manner as in Example 1. As a result, 5.57 mmol of dimethyl carbonate, 0.05 mmol of dimethyl oxalate, 0.13 mmol of methyl acetate and 1.69 mmol of carbon dioxide were formed. Namely, TOF was 139, and CO selectivity was 74%.

EXAMPLE 8

Into an autoclave, the same catalyst composition solution as in Example 6 was charged, and after thoroughly substituting with carbon monoxide, 6.5 kg/cm$^2$ of carbon monoxide was introduced. Then, 105 kg/cm$^2$ of nitrogen gas containing 3.8 vol % of oxygen was injected. The reaction temperature was adjusted to 100° C., and the reaction was conducted for one hour. Then, the reaction system was cooled to room temperature, and the quantitative analysis of the product was conducted in the same manner as in Example 1. As a result, 6.91 mmol of dimethyl carbonate, 0 mmol of dimethyl oxalate, 0.09 mmol of methyl acetate and 1.24 mmol of carbon dioxide were formed. Namely, TOF was 173, and CO selectivity was 84%.

EXAMPLE 9

Into the same autoclave as used in Example 1, 0.04 mmol of palladium acetate, 0.5 mmol of cupric acetate, 1.0 mmol of potassium acetate, 0.5 mmol of 2-hydroxypyridine and 10 ml of methanol were introduced. The interior of the autoclave was thoroughly substituted with carbon monoxide. Then, 10 kg/cm$^2$ of carbon monoxide was introduced. Then, 80 kg/cm$^2$ nitrogen gas containing 3.8 vol % of oxygen was injected. The reaction temperature was adjusted to 100° C., and the reaction was conducted for one hour. Then, the reaction system was cooled to room temperature, and the quantitative analysis of the product was conducted in the same manner as in Example 1. As a result, 2.23 mmol of dimethyl carbonate, 0 mmol of dimethyl oxalate, 0.86 mmol of methyl acetate and 1.70 mmol of carbon dioxide were formed. Namely, TOF was 56, and CO selectivity was 47%.

COMPARATIVE EXAMPLE 5

The reaction was conducted in the same manner as in Example 9 except that no 2-hydroxypyridine was added. As a result, 0.69 mmol of dimethyl carbonate, 0 mmol of dimethyl oxalate, 0.58 mmol of methyl acetate and 1.15 mmol of carbon dioxide were formed. Namely, TOF was 17, and CO selectivity was 29%.

EXAMPLE 10

2 mmol of palladium chloride and 4.4 mmol of sodium chloride were dissolved in 10 ml of methanol, and insoluble matters were filtered off. To the filtrate, 6 mmol of 2-hydroxypyridine was added, and the mixture was stirred. A formed slightly yellow precipitate was collected by filtration, washed with water and hexane and then dried under reduced pressure to obtain 1.7 mmol of bis(2-hydroxypyridine)palladium chloride.

Into the same autoclave as used in Example 1, 0.04 mmol of the bis(2-hydroxypyridine)palladium chloride prepared by the above method, 0.5 mmol of cupric acetate, 1.0 mmol of potassium chloride and 10 ml of methanol were introduced. The interior of the autoclave was thoroughly substituted by carbon monoxide, and then 10 g/cm$^2$ of carbon monoxide was introduced. Then, 80 kg/cm$^2$ of nitrogen gas containing 3.8 vol % of oxygen, was injected. The reaction temperature was adjusted to 100° C., and the reaction was conducted for one hour. Then, the reaction system was cooled to room temperature, and the quantitative analysis of the product was conducted in the same manner as in Example 1. As a result, 9.51 mmol of dimethyl carbonate, 0.27 mmol dimethyl oxalate, 0.08 mmol of methyl acetate and 0.84 mmol of carbon dioxide were formed. Namely, TOF was 238, and CO selectivity was 87%.

EXAMPLE 11

The reaction was conducted in the same manner as in Example 10 except that the reaction time was changed to 30 minutes. As a result, 9.63 mmol of dimethyl carbonate, 0.12 mmol dimethyl oxalate, 0.10 mmol of methyl acetate and 0.73 mmol of carbon dioxide were formed. Namely, TOF was 481, and CO selectivity was 90%.

EXAMPLE 12

The reaction was conducted in the same manner as in Example 10 except that 0.44 mmol of 2-hydroxypyridine was added. As a result, 9.63 mmol of dimethyl carbonate, 0.01 mmol dimethyl oxalate, 0.09 mmol of methyl acetate and 0.71 mmol of carbon dioxide were formed. Namely, TOF was 241, and CO selectivity was 92%.

EXAMPLE 13

The reaction was conducted in the same manner as in Example 10 except that 0.01 mmol of bis(2-hydroxypyridine)palladium chloride was used, and the reaction time was changed to 15 minutes. As a result, 5.16 mmol of dimethyl carbonate, 0.31 mmol dimethyl oxalate and 0.95 mmol of carbon dioxide were formed. Namely, TOF was 2066, and CO selectivity was 75%.

EXAMPLES 14 to 19

The reaction was conducted in the same manner as in Example 13 except that instead of potassium chloride, an alkali metal salt or an alkaline earth metal salt as identified in the following Table 1 was added.

TABLE 1

| Example | Additive | Amount (mmol) | DMC (mmol) | DMO (mmol) | $CO_2$ (mmol) | TOF | CO selectivity (%) |
|---|---|---|---|---|---|---|---|
| 14 | LiCl | 1 | 4.16 | 0.15 | 0.45 | 1663 | 85 |
| 15 | NaCl | 1 | 4.30 | 0.19 | 0.59 | 1719 | 82 |
| 16 | CsCl | 1 | 7.29 | 0.28 | 1.15 | 2916 | 81 |
| 17 | $MgCl_2$ | 0.5 | 1.92 | 0.15 | 0.38 | 770 | 74 |
| 18 | $CaCl_2$ | 0.5 | 1.70 | 0.11 | 0.53 | 680 | 69 |
| 19 | $BaCl_2$ | 0.5 | 4.97 | 0.27 | 1.95 | 1987 | 67 |

DMC: Dimethyl carbonate, DMO: Dimethyl oxalate

EXAMPLE 20

40 mmol of cupric chloride dihydrate was dissolved in 200 ml of ethanol, and a solution having 80 mmol of 2-hydroxypyridine dissolved in 100 ml of ethanol, was added thereto. The mixture was stirred at room temperature, whereby a yellow precipitate precipitated. This precipitate was collected by filtration, washed with ethanol and then dried under reduced pressure to obtain 4.17 g of copper dichloro(2-hydroxypyridine). The result of the elemental analysis was C: 26.38%, H: 2.06%, N: 6.07%, and Cl: 30.76%.

Into the same autoclave as used in Example 1, 0.5 mmol of copper dichloro(2-hydroxypyridine) prepared by the above method, 0.01 mmol of bis(2-hydroxypyridine)palladium chloride, 1 mmol of potassium acetate and 10 ml of methanol were introduced. The interior of the autoclave was thoroughly substituted by carbon monoxide, and then 10 kg/cm² of carbon monoxide was introduced. Then, 80 kg/cm² of nitrogen gas containing 3.8 vol % of oxygen was injected. The reaction temperature was adjusted to 100° C., and the reaction was conducted for 30 minutes. Then, the reaction system was cooled to room temperature, and the quantitative analysis of the product was conducted in the same manner as in Example 1. As a result, 8.54 mmol of dimethyl carbonate, 0.001 mmol of dimethyl oxalate and 0.50 mmol of carbon dioxide were formed. Namely, TOF was 1708, and CO selectivity was 94%.

EXAMPLES 21 to 23

The reaction was conducted in the same manner as in Example 20 except that carbon monoxide and the nitrogen gas containing 3.8 vol % of oxygen (hereinafter referred to as 3.8% $O_2/N_2$) were changed as identified in Table 2.

TABLE 2

| Example | CO (kg/cm²) | 3.8% $O_2/N_2$ (kg/cm²) | DMC (mmol) | DMO (mmol) | $CO_2$ (mmol) | TOF | CO selectivity (%) |
|---|---|---|---|---|---|---|---|
| 21 | 10 | 90 | 10.07 | 0.004 | 0.76 | 2014 | 93 |
| 22 | 5 | 40 | 6.70 | 0.003 | 0.17 | 1340 | 98 |
| 23 | 2 | 18 | 2.32 | — | 0.07 | 463 | 97 |

EXAMPLE 24

The reaction was conducted in the same manner as in Example 22 except that the amount of bis(2-hydroxypyridine)palladium chloride was changed to 0.003 mmol, whereby 5.36 mmol of dimethyl carbonate, 0.016 mmol of dimethyl oxalate and 0.20 mmol of carbon dioxide were formed. Namely, TOF was 3573, and CO selectivity was 96%.

EXAMPLE 25

Copper dichlorobis(2-methoxypyridine) was prepared in the same manner as in Example 20. The results of the elemental analysis were C: 40.27%, H: 3.96% and N: 7.82%. The reaction was conducted in the same manner as in Example 20 except that this copper complex was employed, whereby 7.35 mmol of dimethyl carbonate, 0.28 mmol of dimethyl oxalate and 1.50 mmol of carbon dioxide were formed. Namely, TOF was 1470, and CO selectivity was 78%.

EXAMPLE 26

Copper dichlorobis(4-cyanopyridine) was prepared in the same manner as in Example 20. The results of the elemental analysis were C: 41.40%, H: 2.27% and N: 15.98%. The reaction was conducted in the same manner as in Example 20 except that this copper complex was employed, whereby 6.35 mmol of dimethyl carbonate, 0.26 mmol of dimethyl oxalate and 2.43 mmol of carbon dioxide were formed. Namely, TOF was 1270, and CO selectivity was 68%.

EXAMPLE 27

A complex compound of cupric chloride and 8-hydroxyquinoline was prepared in the same manner as in Example 20. The results of the elemental analysis were C: 44.82%, H: 2.48% and N: 5.65%. The reaction was conducted in the same manner as in Example 20 except that this copper complex was employed, whereby 2.10 mmol of dimethyl carbonate, 0.08 mmol of dimethyl oxalate and 1.00 mmol of carbon dioxide were formed. Namely, TOF was 420, and CO selectivity was 64%.

EXAMPLE 28

A complex compound of cupric chloride and N,N,N',N'-tetramethyl-1,3-propanediamine was prepared in the same manner as in Example 20. The results of the elemental analysis were C: 20.73%, H: 5.59% and N: 6.63%. The reaction was conducted in the same manner as in Example 20 except that this copper complex was employed, whereby 7.96 mmol of dimethyl carbonate, 0.18 mmol of dimethyl oxalate and 1.78 mmol of carbon dioxide were formed. Namely, TOF was 1592, and CO selectivity was 79%.

EXAMPLE 29

A complex compound of cupric chloride and N,N,N',N'-tetramethylethylenediamine was prepared in the same manner as in Example 20. The results of the elemental analysis were C: 28.70%, H: 6.60% and N: 10.96%. The reaction was conducted in the same manner as in Example 20 except that this copper complex was employed, whereby 1.74 mmol of dimethyl carbonate, 0.002 mmol of dimethyl oxalate and 0.25 mmol of carbon dioxide were formed. Namely, TOF was 348, and CO selectivity was 87%.

EXAMPLE 30

40 mmol of cupric chloride dihydrate was dissolved in 260 ml of water, and 20 mmol of quinoxaline was added thereto. Under stirring, the solution became dark green, and 14 ml of 50% hypophosphous acid was added thereto, and the mixture was heated at 90° C. for one hour. A formed brown precipitate was collected by filtration, washed with water and then dried under reduced pressure. The obtained amount was 6.07 g. The results of the elemental analysis were C: 30.00%, H: 1.78% and N: 8.71%. The reaction was conducted in the same manner as in Example 20 except that this copper complex was employed, whereby 3.55 mmol of dimethyl carbonate, 0.07 mmol of dimethyl oxalate and 0.95 mmol of carbon dioxide were formed. Namely, TOF was 710, and CO selectivity was 77%.

EXAMPLE 31

The reaction was conducted in the same manner as in Example 30 except that 1 mmol of potassium acetate and 0.5 mmol of potassium chloride were used instead of 0.5 mmol of potassium acetate, whereby 5.06 mmol of dimethyl carbonate, 0.08 mmol of dimethyl oxalate and 1.37 mmol of carbon dioxide were formed. Namely, TOF was 1012, and CO selectivity was 77%.

EXAMPLE 32

In an autoclave made of Hastelloy C having an internal capacity of 300 ml equipped with an induction stirrer and having a condenser provided at a gas outlet, a glass inner cylinder was placed, and 0.01 mmol of bis(2-hydroxypyridine)palladium chloride, 5 mmol of cupric acetate, 10 mmol of potassium chloride and 100 ml of methanol were introduced thereinto. The interior of the autoclave was substituted by nitrogen, and then 25 kg/cm² of nitrogen gas containing 11.5 vol % of carbon monoxide and 3.3 vol % of oxygen, was injected. The reaction temperature was raised to 100° C., and then a gas mixture of carbon monoxide/oxygen/nitrogen having the above composition was continuously supplied at a rate of 20 l/hr to the autoclave to establish a gas flow system. The reaction was conducted for 4 hours. Then, the reaction system was cooled to room temperature, and the quantitative analysis of the product was conducted in the same manner as in Example 1. As a result, 120 mmol of dimethyl carbonate, 0.45 mmol of dimethyl oxalate, 2.99 mmol of methyl acetate and 29.68 mmol of carbon dioxide were formed. Namely, TOF was 3007, and CO selectivity was 78%.

EXAMPLE 33

Preparation of a Catalyst 2.0 g (11.0 mmol) of anhydrous cupric acetate was dissolved in 75 ml of water, and 50 ml (23.5 g) of active carbon was added thereto, impregnated for 7 hours and then evaporated to dryness. Further, it was dried under nitrogen at 100° C. for one hour and at 200° C. for one hour. 0.39 g (2.2 mmol) of palladium chloride and 0.29 g (4.9 mmol) of sodium chloride were dissolved in 65 ml of methanol, and insoluble matters were filtered off. To the filtrate, the active carbon having cupric acetate supported thereon was added, impregnated overnight and then evaporated to dryness. The obtained solid was added to a solution having 0.63 g (6.6 mmol) of 2-hydroxypyridine dissolved in 70 ml of methanol and impregnated overnight. Then, the solid was collected by filtration, washed with methanol and water and then dried under reduced pressure. Finally, this catalyst was added to a solution of 1.65 g of potassium chloride in 70 ml of water, impregnated for one hour and then evaporated to dryness and further dried under nitrogen at 100° C. for one hour and at 150° C. for one hour.

Preparation of a Carbonic Acid Ester

Into a reactor made of Pyrex glass having an inner diameter of 18 mm and a length of 400 mm, 10 ml of the catalyst prepared by the above method and having 1.0% by weight of palladium metal, 3.0% by weight of copper metal, 1.8% by weight of 2-hydroxypyridine and 7.0% by weight of potassium chloride supported thereon, was packed, and glass beads (particle size: about 2 mm) were packed thereon. This glass beads layer was used as a vaporizer of the alcohol. This reactor was set vertically in an electric furnace. While maintaining the temperature of the catalyst layer at 100° C., a gas mixture comprising 35 vol % of carbon monoxide, 3.9 vol % of oxygen and 61.1 vol % of nitrogen was continuously supplied at a rate of 10 l/hr to the catalyst layer. Further, methanol was likewise supplied at a rate of 10 ml/hr by a microfeeder. The reaction product was collected by a gas-liquid separator, whereupon the collected liquid was analyzed by gas chromatography for a quantitative analysis. On the other hand, the discharged gas was analyzed by gas chromatography to quantitatively analyze carbon dioxide. The reaction was conducted for 2 hours, whereby 19.2 mmol of dimethyl carbonate (hereinafter referred to as DMC), 0.2 mmol of methyl formate (hereinafter referred to as MF), 0.5 mmol of methyl acetate (hereinafter referred to as (MA) and 1.7 mmol of carbon dioxide were formed. Namely, STY was 86.5 g/l/hr, and CO selectivity was 88.9%.

COMPARATIVE EXAMPLE 6

The reaction was conducted in the same manner as in Example 33 except that a catalyst having no 2-hydroxypyridine supported thereon was used, whereby 7.5 mmol of DMC, 0.4 mmol of MF, 0.5 mmol of MA and 5.8 mmol of carbon dioxide were formed. Namely, STY was 33.8 g/l/hr, and CO selectivity was 52.4%.

EXAMPLES 34 and 35

The reaction was conducted in the same manner as in Example 33 except that the reaction temperature was changed as identified in the following Table 3. The results are shown in Table 3 together with the results of Example 33. (In each Example, certain amounts of MF and MA were formed.)

TABLE 3

| Example | Reaction temp. (°C.) | DMC (mmol) | $CO_2$ (mmol) | STY | CO selectivity (%) |
|---|---|---|---|---|---|
| 33 | 100 | 19.2 | 1.7 | 86.5 | 88.9 |
| 34 | 80 | 14.2 | 0.7 | 64.0 | 93.0 |
| 35 | 120 | 21.1 | 3.3 | 95.2 | 83.1 |

EXAMPLE 36

The reaction was conducted in the same manner as in Example 33 using the same catalyst except that 5.9% by weight of copper metal was supported thereon, whereby 27.5 mmol of DMC, 6.4 mmol of carbon dioxide, 0.7 mmol of MF and 1.1 mmol of MA were formed. Namely, STY was 123.9 g/l/hr, and CO selectivity was 77.1%.

EXAMPLE 37

The reaction was conducted in the same manner as in Example 33 using the same catalyst except that 3.5% by weight of potassium chloride was supported thereon, whereby 17.7 mmol of DMC, 0.9 mmol of carbon dioxide, 0.1 mmol of MF and 0.6 mmol of MA were formed. Namely, STY was 79.9 g/l/hr, and CO selectivity was 91.6%.

EXAMPLE 38

The reaction was conducted in the same manner as in Example 33 except that the composition of the gas mixture was changed to $CO/O_2/N_2 = 11\%/5.3\%/83.7\%$, whereby 11.6 mmol of DMC, 0.8 mmol of carbon dioxide, 0.2 mmol of MF and 0.3 mmol of MA were formed. Namely, STY was 52 g/l/hr, and CO selectivity was 89.5%.

EXAMPLE 39

The reaction was conducted in the same manner as in Example 33 except that ethanol was used instead of methanol as the alcohol, whereby 2.2 mmol of diethyl carbonate and 0.4 mmol of carbon dioxide were formed. Namely, STY was 25.5 g/l/hr, and CO selectivity was 85.7%.

EXAMPLE 40

Preparation of a Catalyst 0.8 g (4.4 mmol) of anhydrous cupric acetate was dissolved in 30 ml of water, and 20 ml (9.4 g) of active carbon was added thereto, impregnated overnight and evaporated to dryness. Further, it was dried under nitrogen at 100° C. for one hour and at 200° C. for one hour. 0.32 g (0.88 mmol) of $PdCl_2(2\text{-PyOH})_2$ was suspended in 40 ml of methanol, and the active carbon having the cupric acetate supported thereon, was added thereto, impregnated overnight under stirring and then evaporated to dryness. The catalyst thus obtained was added to 30 ml of an aqueous solution having 0.66 g (8.8 mmol) of potassium chloride dissolved therein, impregnated for one hour and then evaporated to dryness and further dried under nitrogen at 100° C. for one hour and at 150° C. for one hour.

Preparation of a Carbonic Acid Ester

The reaction was conducted in the same manner as in Example 33 except that the catalyst prepared by the above method was employed, and the reaction time was changed to one hour, whereby 6.25 mmol of DMC, 4.1 mmol of carbon dioxide, 0.3 mmol of MF and 0.5 mmol of MA were formed. Namely, STY was 56.3 g/l/hr, and CO selectivity was 63.4%.

EXAMPLE 41

The reaction was conducted in the same manner as in Example 40 except that the carrier was changed to silica, whereby only 0.7 mmol of DMC was formed. Namely, STY was 6.1 g/l/hr, and CO selectivity was 100%.

As described in the foregoing, the present invention provides a method for producing a carbonic acid ester efficiently, and the carbonic acid ester thereby obtained is useful for various applications as a starting material for resins or for medicines or agricultural chemicals. According to the method of the present invention, a combustion loss of carbon monoxide can be reduced to a large extent, and the production rate of the carbonic acid ester can be improved. Further, when the method of the present invention is conducted in a gas phase using the catalyst supported on a carrier, a step of separating the product from the catalyst is not required, which is very important from the industrial point of view.

What is claimed is:

1. A method for producing a carbonic acid ester, which comprises reacting an aliphatic alcohol with carbon monoxide and oxygen in the presence of ①a platinum group metal or its salt, ② metal copper, a copper salt or a copper complex, ③ at least one member selected from the group consisting of alkali metal salts and alkaline earth metal salts, and ④ a 2-hydroxypyridine.

2. A method for producing a carbonic acid ester, which comprises reacting an aliphatic alcohol with carbon monoxide and oxygen in the presence of ① a complex compound made of a platinum group metal or its salt and a 2-hydroxypyridine, ② metal copper, a copper salt or a copper complex, and ③ at least one member selected from the group consisting of alkali metal salts and alkaline earth metal salts.

3. A method for producing a carbonic acid ester, which comprises reacting an aliphatic alcohol with carbon monoxide and oxygen in the presence of ① a complex compound made of a platinum group metal or its salt and a 2-hydroxypyridine, ② metal copper, a copper salt or a copper complex, ③ at least one member selected from the group consisting of alkali metal salts and alkaline earth metal salts, and ④ a 2-hydroxypyridine.

4. A method for producing a carbonic acid ester, which comprises reacting an aliphatic alcohol with carbon monoxide and oxygen in a gas phase in the presence of a solid catalyst having supported on a carrier ① a complex compound made of a platinum group metal or its salt and a 2-hydroxypyridine, ② metal copper, a copper salt or a copper complex, and ③ at least one member selected from the group consisting of alkali metal salts and alkaline earth metal salts.

5. A method for producing a carbonic acid ester, which comprises reacting an aliphatic alcohol with carbon monoxide and oxygen in a gas phase in the presence of a solid catalyst having supported on a carrier ① a platinum group metal or its salt, ② metal copper, a copper salt or a copper complex, ③ at least one member selected from the group consisting of alkali metal salts and alkaline earth metal salts, and ④ a 2-hydroxypyridine.

6. The method according to any one of claims 1 to 5 wherein a platinum group metal is palladium.

7. The method according to claim 1 or 3, wherein the 2-hydroxypyridine is used in an amount of from 1 to $10^4$ mols per mol of the platinum group metal atoms.

8. The method according to claim 2 or 3, wherein the complex compound made of a platinum group metal and a 2-hydroxypyridine, is used in an amount of from 0.001 to 100 mmol per liter of the aliphatic alcohol.

9. The method according to claim 1, wherein the platinum group metal or its salt is used in an amount of from 0.001 to 100 mmol per liter of the aliphatic alcohol.

10. The method according to claim 1, 2 or 3, wherein the metal copper, the copper salt or the complex compound of copper is used in an amount of from 1 to $10^5$ mols per mol of the platinum group metal atoms.

11. The method according to claim 4 or 5, wherein the metal copper, the copper salt or the complex compound of copper is used in an amount of from 1 to 100 mols per mol of the platinum group metal atoms.

12. The method according to claim 5, wherein the 2-hydroxypyridine is used in an amount of from 1 to 103 mols per mol of the platinum group metal atoms.

13. The method according to any one of claims 1 to 5, wherein the platinum group metal or its salt, or a complex compound made of a platinum group metal or its salt and a 2-hydroxypyridine, is supported on a carrier.

14. The method according to claim 4 or 5, wherein the platinum group metal or its salt is supported on the carrier in an amount of from 0.01 to 10% by weight as metal of the platinum group metal, relative to the carrier.

15. The method according to claim 1, 2 or 3, wherein at least one member selected from the group consisting of alkali metal salts and alkaline earth metal salts, is used in an amount of from 1 to $10^5$ mols per mol of the platinum group metal atoms.

16. The method according to claim 4 or 5, wherein at least one member selected from the group consisting of alkali metal salts and alkaline earth metal salts, is used in an amount of from 1 to 103 mols per mol of the platinum group metal atoms.

17. The method according to any one of claims 1 to 5, wherein the 2-hydroxypyridine is 2-hydroxypyridine or 2-hydroxy-6-methylpyridine.

18. The method according to claim 1, 2 or 3, wherein the reaction is conducted in a liquid phase under a condition such that the partial pressure of carbon monoxide is from 1 to 50 kg/cm$^2$, and the partial pressure of oxygen is from 0.1 to 20 kg/cm$^2$.

19. The method according to claim 4 or 5, wherein the reaction is conducted under a condition such that the partial pressure of carbon monoxide is from 0.001 to 20 kg/cm$^2$, the partial pressure of oxygen is from 0.001 to 10 kg/cm$^2$, and the partial pressure of the alcohol is from 0.001 to 20 kg/cm$^2$.

20. The method according to claim 4 or 5, wherein the contact time of carbon monoxide, oxygen and the alcohol with the solid catalyst is from 0.04 to 72 seconds.

* * * * *